(12) United States Patent
Hewett et al.

(10) Patent No.: US 9,307,909 B2
(45) Date of Patent: Apr. 12, 2016

(54) METHOD AND SYSTEM FOR ASSOCIATING AT LEAST TWO DIFFERENT MEDICAL FINDINGS WITH EACH OTHER

(71) Applicants: Andrew John Hewett, Erlangen (DE); Martin Huber, Uttenreuth (DE); Gerhard Kohl, Neunkirchen am Brand (DE); Markus Metz, Weisendorf (DE); Michael Rusitska, Erlangen (DE)

(72) Inventors: Andrew John Hewett, Erlangen (DE); Martin Huber, Uttenreuth (DE); Gerhard Kohl, Neunkirchen am Brand (DE); Markus Metz, Weisendorf (DE); Michael Rusitska, Erlangen (DE)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 71 days.

(21) Appl. No.: 13/742,842

(22) Filed: Jan. 16, 2013

(65) Prior Publication Data

US 2013/0259353 A1 Oct. 3, 2013

Related U.S. Application Data

(60) Provisional application No. 61/617,146, filed on Mar. 29, 2012.

(51) Int. Cl.
  *G06T 7/00* (2006.01)
  *A61B 5/00* (2006.01)
  *G06F 19/00* (2011.01)

(52) U.S. Cl.
  CPC .............. *A61B 5/0033* (2013.01); *A61B 5/0035* (2013.01); *A61B 5/748* (2013.01); *G06F 19/321* (2013.01); *G06F 19/322* (2013.01); *G06F 19/3487* (2013.01); *G06T 7/0012* (2013.01); *G06T 2207/30004* (2013.01)

(58) Field of Classification Search
  None
  See application file for complete search history.

(56) References Cited

U.S. PATENT DOCUMENTS

| | | | |
|---|---|---|---|
| 7,848,553 B2 * | 12/2010 | Hertel et al. .................. | 382/128 |
| 2006/0064321 A1 * | 3/2006 | Sasano et al. ..................... | 705/2 |
| 2006/0277073 A1 * | 12/2006 | Heilbrunn et al. ................ | 705/3 |
| 2007/0064987 A1 * | 3/2007 | Esham .................... | A61B 6/481 |
| | | | 328/128 |

(Continued)

FOREIGN PATENT DOCUMENTS

| | | | |
|---|---|---|---|
| CN | 101408976 A | | 4/2009 |
| CN | 102204846 A | | 10/2011 |

(Continued)

OTHER PUBLICATIONS

Seifert et al., "Hierarchical Parsing and Semantic Navigation of Full Body CT Data," Feb. 2009.

(Continued)

*Primary Examiner* — Utpal Shah
*Assistant Examiner* — Mai Tran
(74) *Attorney, Agent, or Firm* — Harness, Dickey & Pierce, P.L.C.

(57) ABSTRACT

One embodiment of the invention is disclosed, related to a method for associating at least two different medical findings with each other, each of the findings being based on a characteristic area in a different set of images. The location of at least one anatomical landmark in relation to the respective characteristic area is determined in each in each of the different sets of images. Then a reference to the least one anatomical landmark is stored together with the respective finding for each of the at least two findings. Finally, pairs of associated findings based on a comparison of the respective references to the at least one anatomical landmark are identified among the at least two findings.

21 Claims, 4 Drawing Sheets

(56) References Cited

U.S. PATENT DOCUMENTS

| | | | |
|---|---|---|---|
| 2007/0198301 A1* | 8/2007 | Ayers et al. | 705/3 |
| 2008/0260222 A1* | 10/2008 | Kumar | A61B 6/032 382/128 |
| 2009/0087049 A1* | 4/2009 | Takahashi | 382/128 |
| 2010/0076789 A1* | 3/2010 | Pan | 705/3 |
| 2010/0080434 A1 | 4/2010 | Seifert et al. | |
| 2010/0171741 A1 | 7/2010 | Brill et al. | |
| 2011/0179044 A1* | 7/2011 | Crum et al. | 707/749 |

FOREIGN PATENT DOCUMENTS

| | | | | |
|---|---|---|---|---|
| DE | 102009009158 A1 | 9/2010 | | |
| DE | 102009006148 B4 | 11/2010 | | |
| WO | WO 2008151113 A1 | 12/2008 | | |
| WO | WO 2010109351 A1 * | 9/2010 | | G06F 19/00 |
| WO | WO 2011090950 A2 * | 7/2011 | | |
| WO | WO 2011090950 A3 * | 3/2012 | | G06F 19/00 |
| WO | WO 2012123829 A1 | 9/2012 | | |

OTHER PUBLICATIONS

"Annotation and Image Markup (AIM)," https:cabig.nci.nih.gov/community/tools/AIM, Mar. 2012.

"Annotation and Image Markup (AIM)"; cabig.nci.nih.gov/community/tools/AIM, Mar. 2012.

M. Meyer et al: "Probabilistisches Record-Linkage mit anonymisierten Krebsregistermeldungen", httpwww.ekr.med.uni-erlan-gen.de/Papers/WorkshopKrebsregister_2003_RecordLinkage.pdfwww.krebsregister-bayern.de; M. Meyer et al: "Probabilistisches Record-Linkage mit anonymisierten Krebsregistermeldungen", http www.ekr.med.uni-erlang-en.de/Papers/WorkshopKrebsregister_2003_RecordLinkage.pdfwww.krebsregister-bayern.de.

S. Seifert et al: "Hierarchical Parsing and Semantic Navigation of Full Body CT Data", httpstat.fsu.edu/~abarbu/papers/SPIE08_Seifert_Fullbody_04_08_2008.pdf04.08.2008.; S. Seifert et al: "Hierarchical Parsing and Semantic Navigation of Full Body CT Data", httpstat.fsu.edu/~abarbu/papers/SPIE08_Seifert_Fullbody_04_08_2008.pdf04.08.2008.

Sevenster Merlijn et al; "Automatically Correlating Clinical Findings and Body Locations in Radiology Reports Using MedLEE"; Journal of Digital Imaging; the Journal of the Society for Computer Applications in Radiology; Springer Verlag NE; vol. 25; No. 2; pp. 240-249; ISSN 1618-727X; DOI: 10.1007/S10278-011-9411-0; XP035025524; 2011; Jul. 28, 2011.

* cited by examiner

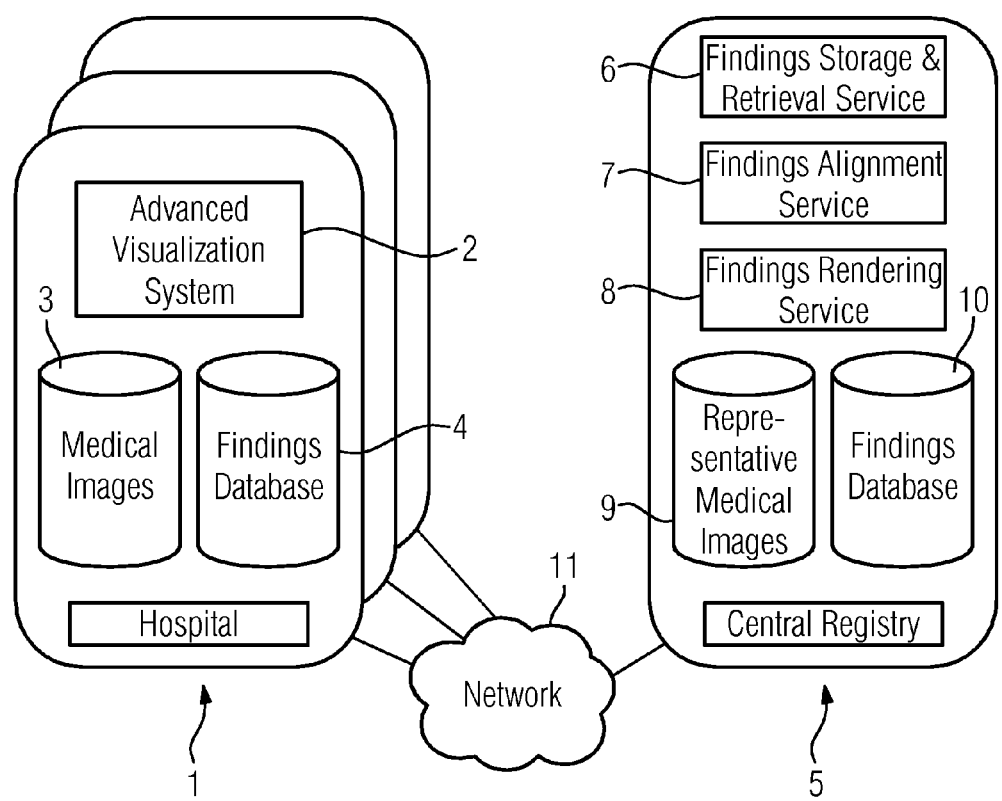

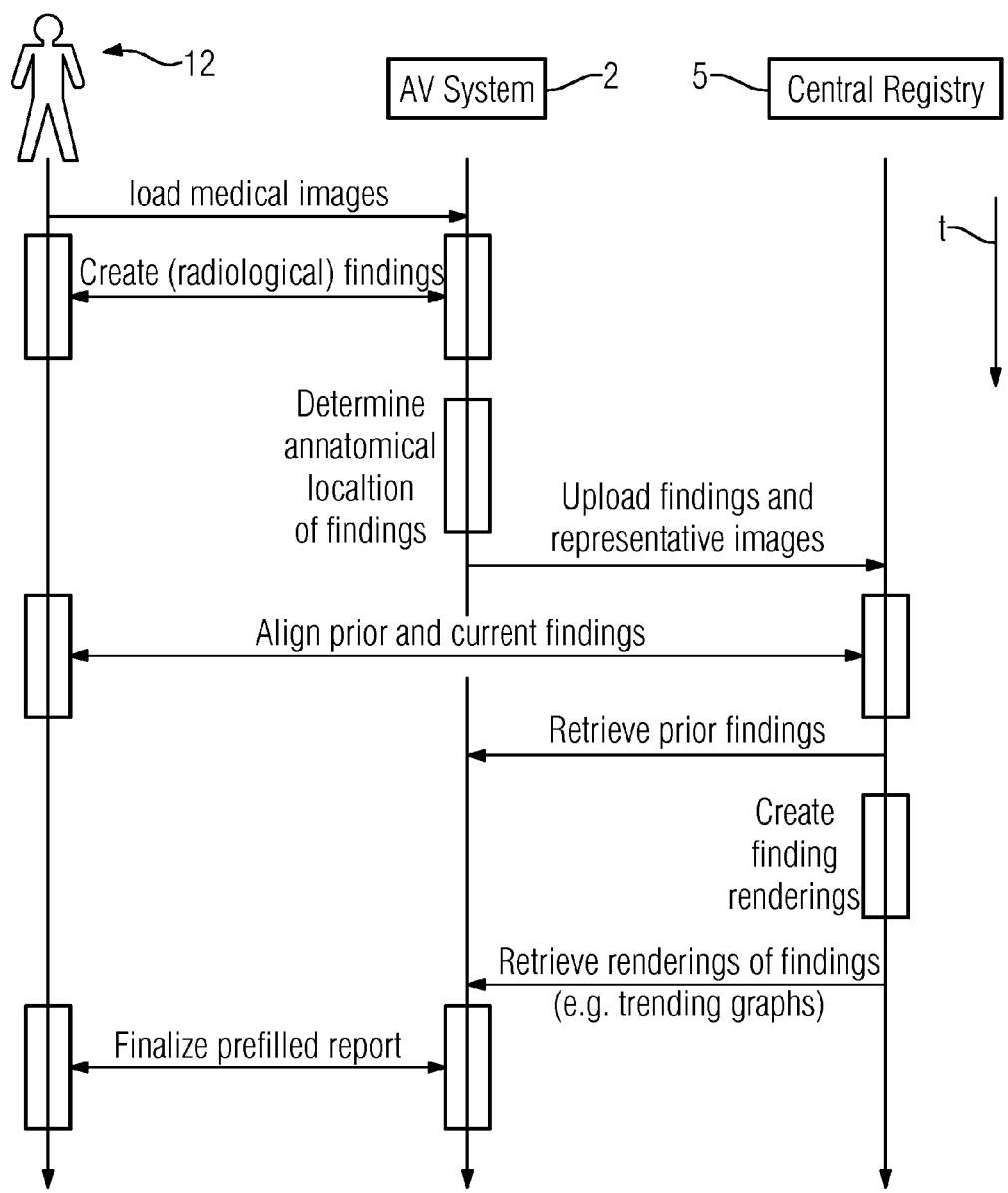

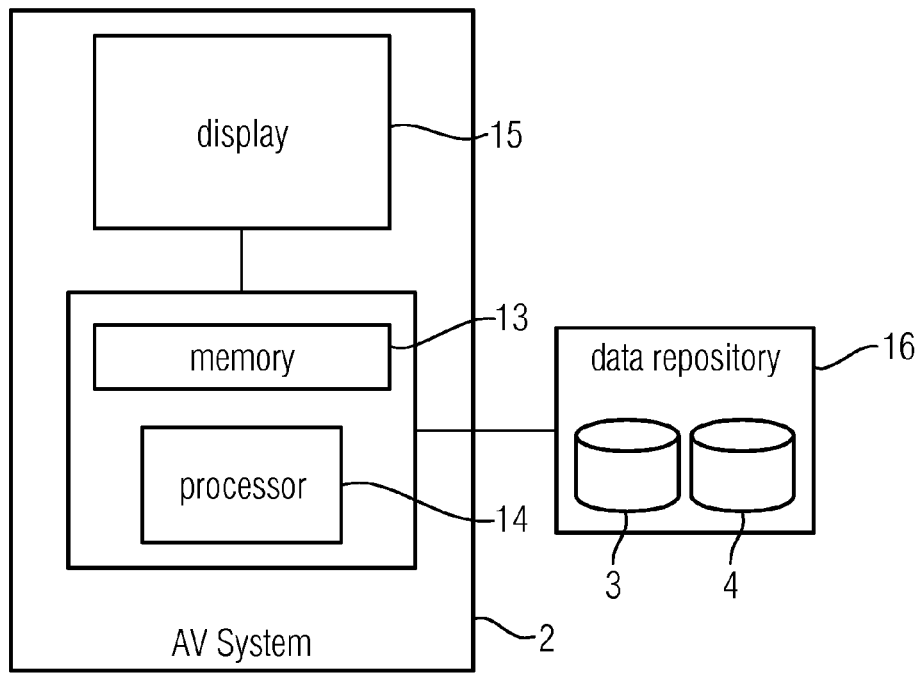
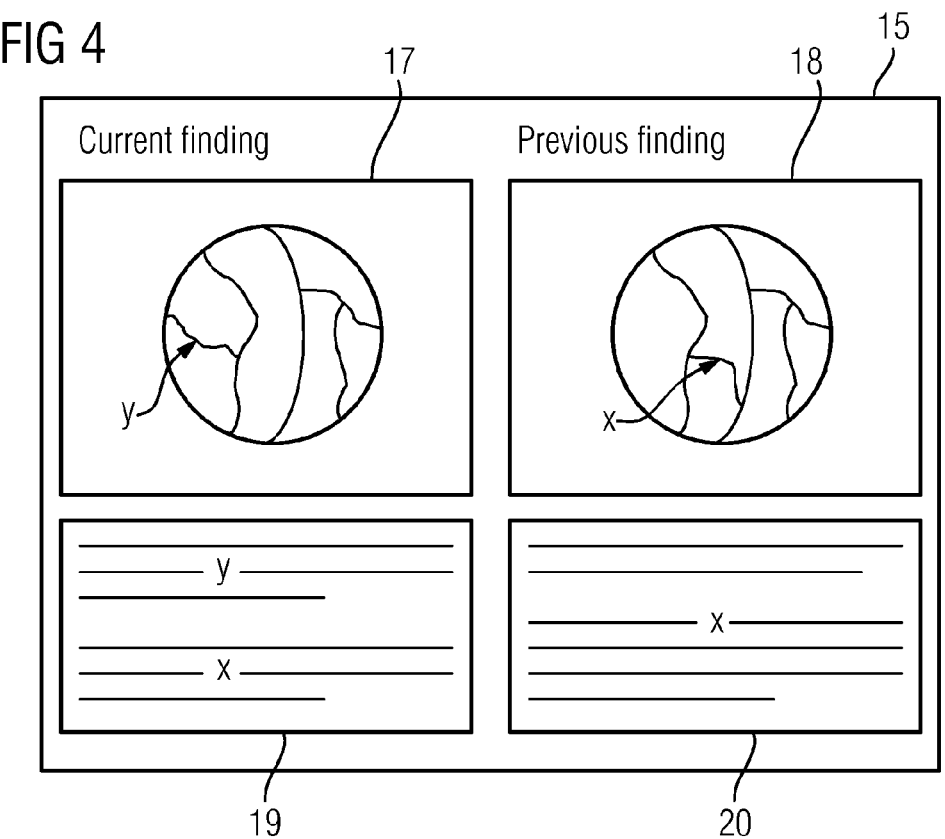

METHOD AND SYSTEM FOR ASSOCIATING AT LEAST TWO DIFFERENT MEDICAL FINDINGS WITH EACH OTHER

PRIORITY STATEMENT

The present application hereby claims priority under 35 U.S.C. §119(e) to U.S. provisional patent application No. 61/617,146 filed Mar. 29, 2012, the entire contents of which are hereby incorporated herein by reference.

FIELD

At least one embodiment of the present invention generally relates to image based medical findings. In particular, at least one embodiment relates to associating different image findings with each other.

BACKGROUND

For many pathologies and diseases, diagnostic images are used for screening, initial diagnosis and treatment follow up. As a result, radiological findings typically are followed over time. Examples of such radiological findings are a liver tumor lesion, a lung nodule, a vessel stenosis, a fatty liver, some infection, an infarct etc. Radiologists rely not only on the latest available images but on the whole history in their decision making. The history might include the time when to intervene, when to change a treatment or when to determine the next follow up interval.

Image examination is often based on a series of medical images acquired by medical image acquisition modalities, such as x-ray device, ultrasound devices, CT or MR scanners. Especially three dimensional image acquisition technologies, such as CT or MR, result in a large number of images. Since medical imaging acquisition often result in hundreds of images, it becomes very time consuming to navigate through the images to identify the image or the small number of images relevant for the medical finding in prior image scans to be able to determine the change of the findings over time. The change of the findings can for example indicate, whether a tumor is growing or a stenos worsening. Accessing historical radiological findings of a patient becomes challenging especially when patients move from one healthcare provider to another.

Medical software applications for accessing findings are known, which document and manage individual radiological findings, for example in a list. It is possible to create and include a new finding into an existing examination file including prior findings. This can be done manually or suggested by the medical software application based on an algorithm. In such a case the new finding can be linked to the closed existing findings based on the three dimensional image volumes which were the basis for the previous and the new finding, respectively.

Different methods of three dimensional registration of image volumes are known. However, these methods require the two image volumes to be registered to be available locally. Since the linking of the new with the previous finding takes place at the time the radiologist reads the new finding, the three dimensional image volume is required to be available locally at this time as well to perform the image registration.

SUMMARY

Often the new and the previous image volumes are stored at different locations. The image volume for the new finding might be available locally at the reading computer system of the radiologist, whereas the previous image volume is stored in a central image database, for example of a Picture Archiving and Communication System (PACS). The previous image volume might also be stored at a remote location with a poor network access or no network access at all. To perform image registration the image volumes need to be made available at the same computer system. This could be either the local computer of the radiologist as well as a remote computer, which might be specifically adapted to perform demanding image processing, such image registration.

The inventors have discovered that there is a need of a method or system which can associate medical findings more easily.

Embodiments of the invention are directed to method(s) and system(s) as described below in different embodiments of the invention.

One embodiment of the invention relates to a method for associating at least two different medical findings with each other, wherein each of the findings being based on a characteristic area in a different set of images. According to this method the location of at least one anatomical landmark in relation to the respective characteristic area is determined in each in each of the different sets of images. Then a reference to the least one anatomical landmark is stored together with the respective finding for each of the at least two findings. Finally, pairs of associated findings based on a comparison of the respective references to the at least one anatomical landmark are identified among the at least two findings.

Another embodiment of the invention relates to a system for associating at least two different medical findings with each other, wherein each of the findings being based on a characteristic area in a different set of images. This system comprises a memory to store the different sets of images, a processor adapted to determine the location of at least one anatomical landmark in relation to the respective characteristic area for each of the different sets of images, a data repository for storing a reference to the at least one anatomical landmark together with the respective finding for each of the at least two findings, and a wherein the processor is further adapted to identify within the at least two findings pairs of associated findings based on a comparison of the respective references to the at least one anatomical landmark.

Another embodiment of the invention relates to a system for associating at least two different medical findings with each other, each of the findings being based on a characteristic area in a different set of images, the system comprises a visualization system and a central registry remote from the visualization system. The visualization system is adapted for accessing different sets of images and adapted to determine in each of the different sets of images the location of at least one anatomical landmark in relation to the respective characteristic area. The central registry comprises a data repository for storing, for each of the at least two findings, a reference to the at least one anatomical landmark together with the respective finding. The central registry is adapted to identify, among the at least two findings, pairs of associated findings based on a comparison of the respective references to the at least one anatomical landmark.

BRIEF DESCRIPTION OF THE DRAWINGS

FIG. 1 shows a hospital and a registry adapted to easily link different findings;

FIG. 2 shows schematically the method steps of a method to easily link different findings;

FIG. 3 shows a system adapted to easily link different findings;

FIG. 4 shows a display with a current finding side-by-side with a previous finding which is related to the current study.

DETAILED DESCRIPTION OF THE PREFERRED EMBODIMENTS

Figure 5:
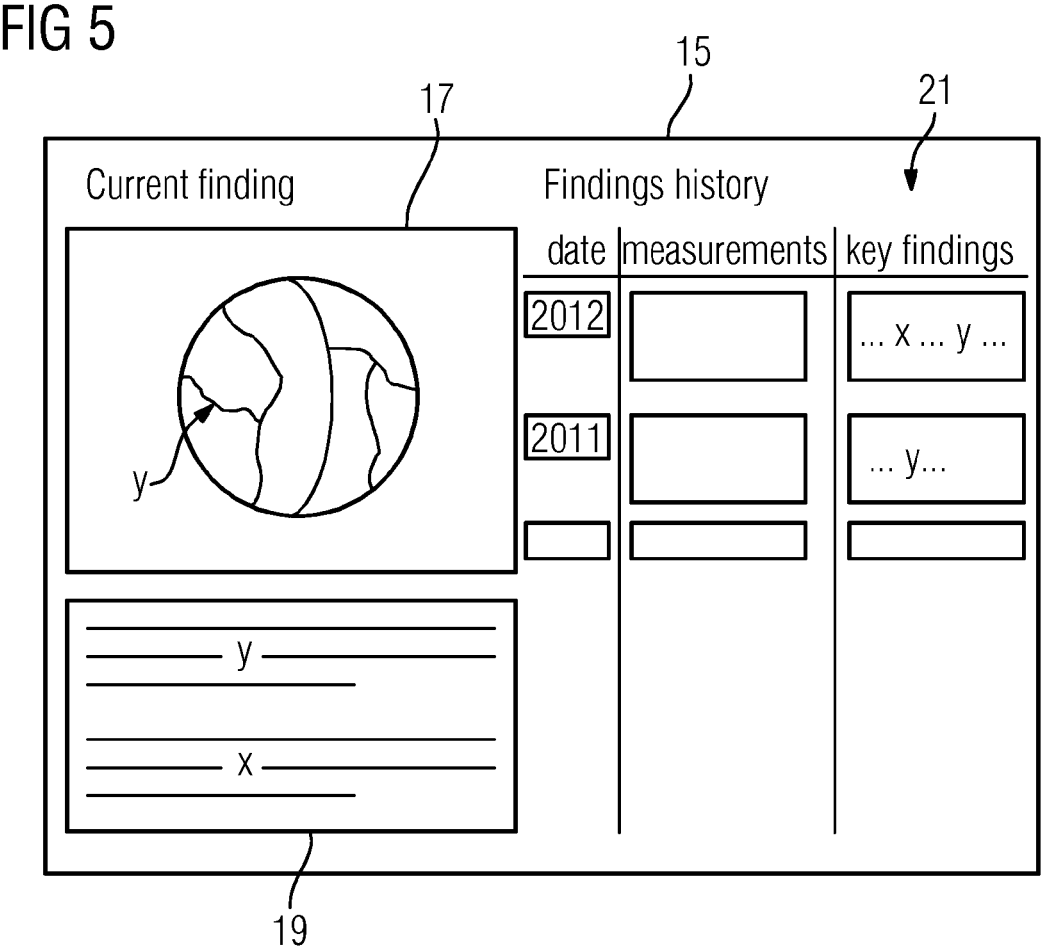
FIG. 5 shows a display with the current finding and a findings history with a tabular overview of related findings.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

Before discussing example embodiments in more detail, it is noted that some example embodiments are described as processes or methods depicted as flowcharts. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Methods discussed below, some of which are illustrated by the flow charts, may be implemented by hardware, software, firmware, middleware, microcode, hardware description languages, or any combination thereof. When implemented in software, firmware, middleware or microcode, the program code or code segments to perform the necessary tasks will be stored in a machine or computer readable medium such as a storage medium or non-transitory computer readable medium. A processor(s) will perform the necessary tasks.

Specific structural and functional details disclosed herein are merely representative for purposes of describing example embodiments of the present invention. This invention may, however, be embodied in many alternate forms and should not be construed as limited to only the embodiments set forth herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

In the following description, illustrative embodiments may be described with reference to acts and symbolic representations of operations (e.g., in the form of flowcharts) that may be implemented as program modules or functional processes include routines, programs, objects, components, data structures, etc., that perform particular tasks or implement particular abstract data types and may be implemented using existing hardware at existing network elements. Such existing hardware may include one or more Central Processing Units (CPUs), digital signal processors (DSPs), application-specific-integrated-circuits, field programmable gate arrays (FPGAs) computers or the like.

Note also that the software implemented aspects of the example embodiments may be typically encoded on some form of program storage medium or implemented over some type of transmission medium. The program storage medium (e.g., non-transitory storage medium) may be magnetic (e.g., a floppy disk or a hard drive) or optical (e.g., a compact disk read only memory, or "CD ROM"), and may be read only or random access. Similarly, the transmission medium may be twisted wire pairs, coaxial cable, optical fiber, or some other suitable transmission medium known to the art. The example embodiments not limited by these aspects of any given implementation.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

One embodiment of the invention relates to a method for associating at least two different medical findings with each other, wherein each of the findings being based on a characteristic area in a different set of images. According to this method the location of at least one anatomical landmark in relation to the respective characteristic area is determined in each in each of the different sets of images. Then a reference to the least one anatomical landmark is stored together with the respective finding for each of the at least two findings. Finally, pairs of associated findings based on a comparison of the respective references to the at least one anatomical landmark are identified among the at least two findings.

Another embodiment of the invention relates to a system for associating at least two different medical findings with each other, wherein each of the findings being based on a characteristic area in a different set of images. This system comprises a memory to store the different sets of images, a processor adapted to determine the location of at least one anatomical landmark in relation to the respective characteristic area for each of the different sets of images, a data repository for storing a reference to the at least one anatomical landmark together with the respective finding for each of the at least two findings, and a wherein the processor is further adapted to identify within the at least two findings pairs of associated findings based on a comparison of the respective references to the at least one anatomical landmark.

Another embodiment of the invention relates to a system for associating at least two different medical findings with each other, each of the findings being based on a characteristic area in a different set of images, the system comprises a visualization system and a central registry remote from the visualization system. The visualization system is adapted for accessing different sets of images and adapted to determine in each of the different sets of images the location of at least one anatomical landmark in relation to the respective characteristic area. The central registry comprises a data repository for storing, for each of the at least two findings, a reference to the at least one anatomical landmark together with the respective finding. The central registry is adapted to identify, among the at least two findings, pairs of associated findings based on a comparison of the respective references to the at least one anatomical landmark.

Medical findings are based on medical observations by a physician or radiologist in certain areas within a set of images. The set of images can for example correspond to a three dimensional image volume. Alternatively it can correspond to images within a two or three dimensional video. Within this set of images a characteristic area will show features which are indicative for a medical finding. This characteristic area can be plainly one individual image within the set of images. It can also be an area of interest within one or more images. Alternatively, the characteristic area can also correspond to a subvolume within the image volume. For medical diagnosis it is helpful to link different findings. To do so, the respective characteristic areas need to be compared.

Instead of relying on a three dimensional image based registration as in the prior art described above, the findings are aligned based on a reference to the anatomical location of the finding in relation to a set of body landmarks. The references are in relation to said characteristic areas, e.g. the landmarks can be within or close by the respective characteristic area. The individual steps of an example embodiment are described below.

By way of detection algorithms, the location of various anatomical landmarks and anatomical structures can be determined. One example of such algorithm is described in the US patent application with the publication number 2010/0080434 A1, the entire contents of which are hereby incorporated herein by reference. Another example is presented in the article "Hierachical Parsing and Semantic Navigation of Full Body CT Data" by Seifert et al. (see http://stat.fsu.edu/~abarbu/papers/SPIE08_Seifert_Fullbody_04_08_2008.pdf), the entire contents of which are hereby incorporated herein by reference. The reference can very easily be provided with respect to landmarks in form of the 33 human vertebrae, since the location of these vertebrae can easily be determined.

A finding can be a text description of observations made by a radiologist or another other physician. A finding might include terminology or coordinates to identify the characteristic area within the set of images.

If a finding is created, either manually or automatically, the closest landmarks are determined. This can be done by measuring the distance from the landmarks to the characteristic area in three dimensional image volume. Especially, the closest landmarks, e.g. in form of vertebrae, are determined. Also, the laterality of the finding is determined, for example by comparing y coordinate of finding with determined so-called midline.

Typical anatomical landmarks are located at bones, vessels and organs. Bones can be, for example, the attachment of the ribs to the vertebrae and the sternum, the leftmost (rightmost) points of the left (right) ribs, the most caudal point of the sternum. Vessels can be, for example, most cranial point of aortic arch, vessel bifurcations like the renal arteries branching from the descending aorta. Organs can be, for example, the hilum of the kidneys.

The so-called semantic coordinates, e.g. distance and direction to the closest landmarks, determined in the previous step are added to the finding details as reference to the relevant landmarks. The semantic coordinates typically consisting of some identification, a name or label, some type information, measurements, some acquisition parameters, and other observations entered by the radiologist or determined by an advanced visualization system. The semantic coordinates are stored either in the image file of one or multiple images that best represent the finding, e.g. in the DICOM header, or they are stored as a separate file in the context of the set of images, e.g. in form of an image study. For example, information regarding the closest vertebrae could be stored as "level=T3" or "level=T4/T5" if the finding is on the level of T3 or between T4 and T5 respectively. As a language for storing such image annotations, one can use for example so-called Annotation and Image Markup AIM (see https://cabig.nci.nih.gov/community/tools/AIM), the entire contents of which are hereby incorporated herein by reference.

Further details of example embodiments are described in reference to the figures.

FIG. 1 shows a system for associating at least two different medical findings with each other, wherein each of the findings are based on a characteristic area in different sets of images. The system includes one or more advanced visualization (AV) system 2 installed in one or more hospitals 1, which are connected to a remote central registry 5 via a network connection 11. The network 11 can be an internet connection or any other suitable kind of network allowing the exchange of data.

The AV system 2 comprises one or more computers, each with at least one monitor for displaying data, e.g. medical images, a processor, RAM, a keyboard and a computer mouse. At the hospital 1 a local network can be established linking the AV system 2 with medical imaging devices, such as magnetic resonance (MR), computer tomography (CT) or x-ray imaging devices. These devices are adapted to acquire medical images in form of 3D data sets. These 3D data sets usually comprise a series of cross-sectional or projection images of a patient. The medical images are stored in a medical image storage 3, which is part of the hospital network at the hospital 1.

The AV system 2 is used to display the medical images for diagnosis and review. The medical images can be delivered directly from the medical imaging device or from the medical image storage 3. Additionally the AV system 2 may include software for pre- or post-processing of the medical images to identify and enhance features which are relevant for the medical diagnosis. This includes quantitative image analysis, e.g. measurements of lengths, size and shape of anatomical features with the medical image.

Based on the review of a set of medical images of a patient and the quantitative image analysis findings are prepared at the AV system 2. These findings include medical observations, for example as text with reference to certain aspects to the particular set of images. The findings may also include a representative image or a small set of representative images. These findings can be stored in the findings database 4 which is also connected to the hospital network. The findings are typically prepared by a radiologist who is experienced in reading the particular kind of medical image data.

Finally the AV system 2 is adapted to be used to create a final report taking into account current any often also earlier findings. The report may, for example, be prepared by a radiologist for a referring physician.

The hospital network may comprise more than one AV system 2, which is used by different physicians or different departments within the hospital 1. Different AV systems 2 may also have dedicated purposed, e.g. one AV system 2 might be used for quantitative image analysis, another AV system 2 might be used for findings creation and another AV system 2 might be used for report creation.

The functions of the AV system 2 are mostly determined by a set of dedicated software applications for quantitative image analysis, finding creating and report creation.

The steps of determining the location of anatomical landmarks in relation to the representative area in the set of images and determining corresponding semantic coordinates can, for example, be performed in the hospital with the AV system 2 in cooperation with medical images from the medical image storage 3 and the findings database 4 as shown in FIG. 1. The medical images storage 3 and findings database 4 can be integrated in the AV system 2 or it can be separate.

To sum up the method steps on the side of the hospital, Quantitative imaging findings are created with an advanced visualization (AV) system 2 and persisted using the Annotation and Image Markup (AIM) format. Whenever available the anatomical location of the finding as well as corresponding representative images are part of the AIM representation.

The enhanced finding details and optionally the most representative image(s) including the characteristic area are transferred to the central registry 5, which includes a data repository. Optionally, pseudo-anonymization as used for example by epidemiological cancer registries is applied to the data set before sending it to the registry 5. The central registry 5 includes in this embodiment a findings storage & retrieval service 6, a findings alignment service 7, a storage for representative medical images 9 and a findings database 10 as data repository.

As mentioned before, findings from the AV system 2 of one or more hospitals 1 are transferred to the central registry 5. Hence findings can be saved both in the finding database 4 of a hospital 1 and a finding database 10 of the central registry 5. However, a hospital 1 will usually only save findings which are of relevant for diagnosis and treatment of patients of this hospital 1, whereas the central registry 5 will collect and store for a long period, e.g. for several years or even decades, of many hospitals 1. Since the findings are saved in the central registry 5, they may be deleted in the findings database 4 of the hospital 1 after a predetermined period, e.g. a few weeks or months, have past. The full sets of medical images of a particular study of a patient which is the basis for specific findings will only be saved in the local image storage 3 of the hospital 1 and not transferred to the central registry 5. If at all, only a few selected representative images for each study will be transferred to the central registry 5 for long term storage, thereby significantly reducing the amount of data saved at the central registry 5 compared to the hospital 1. These representative images need not to be saved separately at the hospital 1, at which the findings can simply include a reference to the representative images in the full set of medical images.

Via the central registry 5 the findings and optionally the respective representative medical images are made available not only to the hospital 1 from which they originated, but also to other hospitals 1 which might need them for reference and comparison. Hence, the central registry 5 works as a central hub for long term storage and distribution of findings and representative images. Of course, law and regulations for data protection and privacy need to be addressed by known device(s) of access control.

The central registry 5 is computer server system, which is located remote from the AV system 2. In fact, the central registry 5 could be located anywhere in the world as long as the network 11 to the AV systems 2 can be established with sufficient band width. Since the regulation for handling patient specific healthcare information are often different from country to county, it might be preferable to locate the central registry 5 in the same country as the AV systems 2 which need to have access to the central registry 5. The central registry 5 may comprise a single server or several servers, which can be located in proximity to each other or which can be distributed over several locations and virtually linked to one system. Each server will comprise a processor and RAM and will be linked to a data repository of significant capacity, e.g. several terabyte of storage capacity.

In addition to saving findings and optionally representative images, the central registry 5 may be enhanced with additional service modules, which provide services that can be used by the AV system 2. The service modules can be made available as so-called web services, i.e. software modules which use internet technology to provide service functions. The web services might be made available for a user of the AV system 2 by means of an internet browser and an internet access to the central registry 5.

In the embodiment illustrated in FIG. 1 three different web services are included:
- a findings storage & retrieval service 6 which enables the central registry 5 to receive findings over the network 11, store them in the findings database 10 and make them available for retrieval via the network 11, e.g. to the AV system 2;
- a findings alignment service 7 which identifies pairs of associated findings—in other word, which aligns findings—based on the reference to the area of interest in relation to the anatomical landmarks, e.g. in semantic coordinates; and
- a findings rendering service 8 which creates a representation—or history—of associated findings in form of a table or a trending graph and sends it to the AV system 2.

The function of the finding alignment service 7 and the finding rendering service 8 can be partly or completely taken over by the AV system 2 as long as the required data is made available by the central registry 5.

These and other services provided by the central registry 5 are described in more details below.

In the central registry 1, the latest prior radiological study for the patient is identified and the findings of the current study are linked to, i.e. associated with, the findings of the latest prior study by the findings alignment service 7 and therefore to all prior studies assuming the same procedure was used in the past as follows:
- The findings are sorted independently for the prior and the current study. The order can be determined cranial—caudal based on the cranial—caudal order of the used anatomical landmarks. For example the information about the closest vertebrae determined before can be used, further ordering findings on the same level from left side to the right side. This step is performed by the findings alignment service 7 and the result made available via the network 11 to a user of the AV system 2.
- The user of the AV system 2 is presented with the ordered findings side by side. For each finding the available information like name and observations is displayed as well as, if available, corresponding reference images. In a concrete implementation, the two sorted lists are displayed in two columns starting with the most cranial findings for each study. The word "study" and many other terms specific to healthcare IT are used as defined in the DICOM standard for Digital Imaging and Communication in Medicine.

In an example embodiment, for each pair of a finding in the prior study and a finding in the current study, a probability is calculated that the two findings describe the same pathology, for example taking into account the proximity of findings to landmarks, whether they are of the same type and how similar other parameters are. This step is also performed by the findings alignment service 7.

In an example embodiment, starting with the pairs who most likely describe the same findings, such pairs are aligned/linked until a certain threshold is reached and the remaining findings are considered "orphans", for example a new lesion that was not present earlier or an old lesion that was surgically removed.

In another example embodiment, linked pairs or orphans are displayed side by side in cranial—caudal order.
- An Information about the identified pair of associated findings is sent from the central registry 5 to the AV system 2 and displayed to the user. The user accepts the suggested alignments or links, or manually aligns or links other pairs. This acceptance or realignment is finally sent back to the central registry 5 and saved in association with the findings database 10.

All available information about each associated finding is transferred back to the advanced visualization system 2. The advanced visualization system 2 can now render the historical findings data e.g. in tables or trending graphs. Alternatively, such renderings are provided as a web service 8 by the central registry 5.

Thus, we propose uploading findings information, e.g. as AIM files, including few representative images including the characteristic area of interest to the central vendor neutral registry 5 that provides further services to align findings over time, if previous findings exist for the same patient. Heuristics are applied to align the findings. Next, prior and current findings are presented side by side in cranial-caudal order to the user who validates the alignment. For dedicated findings the registry 5 offers specialized renderings of the findings history as tables and trending graphs.

The schematic representation of the hospital and the registry in FIG. 1 operates as described step by step below.

The user, e.g. the radiologist, loads medical images stored in the medical image storage 3 in or linked to the AV system 2.

User reads the case and creates radiological findings, e.g. measurements like diameter of aorta, volume of a tumor, degree of a stenosis. Additional findings can be generated by the AV system 2, e.g. utilizing computer aided detection algorithms. User and/or AV system 2 determine the anatomical location of the findings (in general relative to known anatomical structures or landmarks).

The findings, including their anatomical locations and representative images, are stored locally in the findings database 4 and uploaded to the central registry 5 using e.g. a web service 6. Findings and representative images are stored in the storage for representative images 9 and in the findings database 10 of the central registry 5, respectively.

The user now validates the alignment of the current findings with prior findings of the same patient. Based on heuristics, the findings alignment service 7 suggests alignments that the user can accept, change or reject. To support the validation representative images for prior and current findings are displayed. As a result, it is also known which findings are new and which findings disappeared.

Optionally, prior findings, including representative images are sent to the AV system 2.

The findings rendering service 8 creates visual representations of the progression of the findings in form of table (e.g. listing prior sizes, current sizes, changes) or trending graphs that can be accessed by the AV system 2.

The AV system 2 prefills a radiology report with the findings data created before and the renderings of the historical finding data retrieved from the registry 5. The radiologist completes the report, e.g. by dictating further observations and his/her impression.

FIG. 2 shows the method steps and the relation of respective components performing the steps. This figure is divided in three columns, in which the left column refers to a user of the AV system 2, the middle column refers to the AV system 2 itself and the right column refers to the central registry 5. The steps are performed in the order from the top to the bottom of the figure. Arrows between the columns indicate interactions or data exchange between the three entities.

At first the user 12 loads medical images into the AV system 2. The medical images may be directly received from a medical image system or the medical image storage 3. The user 12 creates the (radiological) finding at the AV system 2, which then determines the anatomical location of the findings as described above.

The AV system 2 uploads this finding and representative images via the network 11 to the central registry 5. The central registry 5 receives these data and saves it in the storage for representative medical images 9 and the findings database 10 with the help of the findings storage & retrieval service 6.

The findings alignment service 7 of the central registry 5 identifies one or more prior findings which are associated with the current finding based on the respective anatomical location. A proposed alignment is displayed to the user 12 for validation.

After validation of the alignment the one or more related prior findings are transferred from the central registry 5 to via the network 11 to the AV system 2. The AV system 2 displays the current and the related prior studies side-by-side to the user 12 for comparison.

Optionally, the finding rendering service 8 of the central registry 5 may create representations of the history of related findings, e.g. as a table or trending graph. This representation—or "rendering"—is transferred from the central registry 5 via the network 11 to the AV system 2 and displayed to the user 12.

The AV system 2 creates a medical report based on a template which is prefilled with data provided by the central registry 5 in this context, including from prior findings. Based on this prefilled report the user 12 finalized the medical report at the AV system 2.

The method is independent of the modalities used to acquire the medical images. For example the prior study could have been acquired with a CT scanner of vendor A and the reading could have done with an advanced visualization system 2 of vendor B whereas the current study was acquired with a MR scanner of vendor C and the reading is done with an advanced visualization system 2 of vendor D (as long as both advanced visualization systems 2 support the suggested method).

The method can identify one or more than one pair of related findings. The findings can be represented by one characteristic image including the characteristic area.

FIG. 3 shows a simplified embodiment of the invention which does not require a central registry 5 as mentioned before. In this embodiment the functions of the central registry 5 are incorporated in the AV system 2. The AV system 2 comprises a memory 13 for temporarily storing sets of images, a processor 14 adapted to determine in the location of anatomical landmarks in relation to the characteristic area on which the findings are based and a data repository 16 for storing a reference to the at least one anatomical landmark together with the respective findings. The processor 14 is further adapted to identify pairs of associated findings based on a comparison of the respective reference to the at least one anatomical landmark in a similar manner as described in reference to the previous embodiments.

The system 2 further comprises a display 15 for displaying the medical image related to the current and optionally related to previous findings stored in the data repository 16. These images can be displayed side-by-side on the display 15.

The data repository 16 includes both the medical image storage 3 and the findings database 4. In this embodiment the findings database is adapted for long term storage of the findings in the same fashion as the findings database 10 of the central registry 10 described in the context of the previous embodiment.

The additional functions of central registry 5 of the embodiments before, i.e. the findings alignment service and the finding rendering service, are taken over by AV system 2 as well.

FIG. 4 shows how the AV system 2 according to the aforementioned embodiments may display current findings side-by-side with related previous findings after the alignment is completed.

The current finding on the left includes a representative image 17 of an anatomical structure, e.g. a heart. Based on the anatomical landmarks in relation to the characteristic area in this representative image 17 previous findings were identified and corresponding data provided by the central registry 5 to be displayed by the AV system 2. The previous findings also include a representative image 18 including the same characteristic area. The previous image 18 is displayed as part of the previous findings on the right hand side of the display 15.

The text content 19 and 20 of the respective findings are displayed in the half of the display 15 beneath the respective representative images. The images 16 and 17 include annotations x and y which are referred to in the findings 19 and 20.

FIG. 5 shows the display 15 with the current study on the left hand side as in FIG. 4 and a table with the findings history 21. This is prepared by the finding rendering service 8 of the central registry 5 as described before. The findings history 21 contains an overview of previous findings which were identified as related to the current finding.

We demonstrated in a research setting that a central registry 5 of findings allows radiologists to semi-automatically align findings over time providing a finding history even if prior imaging studies are not available locally. Furthermore, a web service 8 provides tabular and graphical renderings for longitudinal quantitative lesion measurements that can be embedded or attached to a radiology report. To apply such a system in clinical routine, an appropriate organization needs to take responsibility for such a registry 5.

Radiological findings can be centrally managed based on the Annotation and Image Markup (AIM) format. Integrating basic web services to store findings, to validate their alignments and to retrieve prior findings into an AV system 2 allows radiologists to better judge the course of a disease and to add relevant longitudinal information to the radiology report.

At least one embodiment of the inventions overcomes the current limitation of requiring full 3D image data sets to align/link radiological findings. Since 3D image data sets typically range in the order of several hundred megabytes, it is unfeasible to store all 3D image data sets of all patients centrally. On the other hand, patients do visit different healthcare providers over time and it is a frequent scenario that old image data sets are missing and not available. Even if the prior data is available e.g. on a CD or some remote server, the time required to import the data to the advanced visualization system is prohibitive in a busy radiological setting. Only a few meta data are sent to some central (or at least regional) registry 5 optionally complemented by one or very few images most representative for the radiological finding. It should also be noted, that even in the ideal case of having all 3D image studies available on the advanced visualization system, the user preferably has to accept any linking/alignment suggested by the system.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, tangible computer readable medium and tangible computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a tangible computer readable medium and is adapted to perform any one of the aforementioned methods when run on a computer device (a device including a processor). Thus, the tangible storage medium or tangible computer readable medium, is adapted to store information and is adapted to interact with a data processing facility or computer device to execute the program of any of the above mentioned embodiments and/or to perform the method of any of the above mentioned embodiments.

The tangible computer readable medium or tangible storage medium may be a built-in medium installed inside a computer device main body or a removable tangible medium arranged so that it can be separated from the computer device main body. Examples of the built-in tangible medium include, but are not limited to, rewriteable non-volatile memories, such as ROMs and flash memories, and hard disks. Examples of the removable tangible medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for associating at least two different medical findings with each other, the method comprising:

determining, in a first of a plurality of different sets of images, a location of at least one anatomical landmark based on a first of the at least two different medical findings in a characteristic area of the first of the plurality of different sets of images, each of the at least two different medical findings including observations made by a radiologist or other physician based on examination of the characteristic area in a set of images among the plurality of different sets of images;

storing, at a memory for the first of the at least two different medical findings, a reference to the at least one anatomical landmark together with the first of the at least two different medical findings;

comparing, at a processor of a central registry, the stored reference to the at least one anatomical landmark with stored references to anatomical landmarks associated with others of the at least two different medical findings; and identifying, at the processor of the central registry, at least one second medical finding associated with the first of the at least two different medical findings, from among the others of the at least two different medical findings, based on the comparison.

2. The method according to claim 1, wherein the reference to the at least one anatomical landmark includes at least one of a distance and a direction of the at least one anatomical landmark with respect to the characteristic area.

3. The method according to claim 1, further comprising:
uploading the reference to the at least one anatomical landmark together with the first of the at least two different medical findings from a visualization system to a central registry remote from the visualization system, wherein the reference to the at least one anatomical landmark together with the first of the at least two different medical findings are stored by the central registry, and the at least one second medical finding is identified by the central registry.

4. The method according to claim 3, wherein the location of the at least one anatomical landmark is determined with the visualization system.

5. The method according to claim 3, further comprising:
providing, by the visualization system, an option to select one or more representative images to be included in the first of the at least two different medical findings.

6. The method according to claim 3, further comprising:
making the at least two different medical findings available, by the central registry, for retrieval by the visualization system.

7. The method according to claim 3, further comprising:
presenting, by the visualization system, the associated first and second medical findings side by side.

8. The method according to claim 3, further comprising:
calculating, by the central registry, a probability indicative of a medical relation of the associated first and second medical findings.

9. The method according to claim 3, further comprising:
sending, by the central registry, information about the associated first and second medical findings to the visualization system;
displaying, by the visualization system, the information about the associated first and second medical findings to a user for validation.

10. The method according to claim 9, wherein the associated first and second medical findings are made available at the visualization system for manual realignment to form a new pair of associated medical findings.

11. The method according to claim 3, further comprising:
creating, by the central registry, a representation of the associated first and second medical findings in the form of at least one of a table and a trending graph; and
sending the representation to the visualization system for display.

12. The method according to claim 11, wherein the representation is based on a history of all associated medical findings stored in the central repository.

13. The method according to claim 3, further comprising:
prefilling, by the visualization system, a radiology report based on the associated first and second medical findings.

14. The method according to claim 11, further comprising:
prefilling, by the visualization system, a radiology report based on the representation of the associated first and second medical findings created by the central registry.

15. A system for associating at least two different medical findings with each other, the system comprising:
a memory configured to store a plurality of different sets of images;
a processor configured to determine, in a first of the plurality of different sets of images, a location of at least one anatomical landmark based on a first of the at least two different medical findings in a characteristic area of the first of the plurality of different sets of images, each of the at least two different medical findings including observations made by a radiologist or other physician based on examination of the characteristic area in a set of images among the plurality of different sets of images; and
a data repository configured to store, for the first of the at least two different medical findings, a reference to the at least one anatomical landmark together with the first of the at least two different medical findings;
the processor being further configured to
compare the stored reference to the at least one anatomical landmark with stored references to anatomical landmarks associated with others of the at least two different medical findings, and
identify, among the others of the at least two different medical findings, at least one second medical finding associated with the first of the at least two different medical findings based on the comparison.

16. A system for associating at least two different medical findings with each other, the system comprising:
a visualization system having a processor and a memory, the visualization system being configured to
access a plurality of different sets of images, and
determine, in a first of the plurality of different sets of images, a location of at least one anatomical landmark based on a first of the at least two different medical findings in a characteristic area of the first of the plurality of different sets of images, each of the at least two different medical findings including observations made by a radiologist or other physician based on examination of the characteristic area in a set of images among the plurality of different sets of images; and
a central registry remote from the visualization system, the central registry including a data repository configured to store, for the first of the at least two different medical findings, a reference to the at least one anatomical landmark together with the first of the at least two different medical findings,
wherein the central registry is configured to
compare the stored reference to the at least one anatomical landmark with stored references to anatomical landmarks associated with others of the at least two different medical findings, and
identify, among the others of the at least two different medical findings, at least one second medical finding associated with the first of the at least two different medical findings based on the comparison.

17. The system according to claim 16, further comprising:
a network, configured to upload at least one of the reference to the at least one anatomical landmark and the first of the at least two different medical findings from the visualization system to the central registry.

18. The system according to claim 17, wherein central registry includes at least one of:
a web service configured to make medical findings available for retrieval by the visualization system;
a web service configured to send information about the associated first and second medical findings to the visualization system for validation by a user; and
a web service configured to create a representation of the associated first and second medical findings in form of at least one of a table and a trending graph, and configured to send the representation to the visualization system.

19. The system according claim 16, wherein the visualization system further comprises:
   a display configured to present the associated first and second medical findings side by side.

20. The system according to claim 16, wherein the visualization system is adapted to prefill a radiology report based on the associated first and second medical findings.

21. The method of claim 1, wherein each of the at least two different medical findings include possible diagnoses based on examination of the characteristic area in the set of images among the plurality of different sets of images by the radiologist or other physician.

* * * * *